United States Patent [19]

Hofinger et al.

[11] Patent Number: 4,606,916
[45] Date of Patent: Aug. 19, 1986

[54] QUATERNARY OXALKYLATED POLYESTERS, A PROCESS FOR THEIR PREPARATION AND THEIR USE

[75] Inventors: Manfred Hofinger, Burgkirchen; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 680,982

[22] Filed: Dec. 12, 1984

[30] Foreign Application Priority Data

Dec. 14, 1983 [DE] Fed. Rep. of Germany ....... 3345156

[51] Int. Cl.[4] .......................... A61K 7/06; A61K 7/08; C07C 67/08; C07C 69/34
[52] U.S. Cl. ...................................... 424/70; 560/88; 560/196

[58] Field of Search ..................... 560/196, 88; 424/70

[56] References Cited

U.S. PATENT DOCUMENTS 2,944,025  7/1960  Verdol ............................ 560/196 X Primary Examiner—Natalie Trousof
Assistant Examiner—Vera C. Clarke
Attorney, Agent, or Firm—Connolly and Hutz

[57] ABSTRACT

Novel quaternary oxalkylated polyesters prepared from oxalkylated fatty amines by polycondensation with a dicarboxylic acid and subsequent reaction with an alkylene oxide and a carboxylic acid or a mineral acid or with a quaternizing agent such as methyl chloride, are described. The compounds are suitable for use as cosmetic active compounds, in particular for cosmetic care of the hair.

6 Claims, No Drawings

QUATERNARY OXALKYLATED POLYESTERS, A PROCESS FOR THEIR PREPARATION AND THEIR USE

Human hair can be attacked and damaged, in some cases irreparably, by external influences, in particular by physical, chemical and biological influences. In addition to other agents, quaternary ammonium compounds have been widely employed in hair rinses for prophylaxis, for reducing influences of this type and for cosmetic treatment of the hair after washing. Substantive quaternary ammonium compounds of this type make it possible to achieve the desired conditioning effects on the hair, which are to be understood as meaning, above all, easier facility for combing the hair when wet and dry and a soft feel and volume and fullness in the washed hair. Examples of such quaternary ammonium compounds are alkyltrimethylammonium halides, dialkyldimethylammonium halides, alkyldimethylbenzylammonium halides (alkyl being understood here as meaning in each case a long-chain fatty alkyl radical), oxalkylated quaternary ammonium compounds and heterocyclic quaternary ammonium compounds, such as, for example, imidazolinium or morpholinium compounds.

In order to reduce the series of operations required when hair rinses are used, attempts have also already been made to incorporate quaternary ammonium salts into hair shampoos. In so doing, however, so-called electroneutral salts, which can only produce the desired conditioning effects on the hair to a very reduced extent are formed together with the anionic surfactants which are usually present in shampoos.

An improvement is afforded by the use of polymeric quaternary ammonium salts in hair shampoos. These are, for example, cellulose derivatives which carry quaternary ammonium groups and are known, for example, from U.S. Pat. No. 3,472,840; also, in particular, polyvinylpyrrolidones or copolymers of vinylpyrrolidone with acrylates or methacrylates (cf., for example, German Offenlegungsschrift No. 2,103,898) which carry quaternary ammonium groups; or copolymers of dialkenyldialkylammonium salts and acrylamide or methacrylamide, such as are described in German Offenlegungsschrift No. 3,029,306.

The use of such high-molecular quaternary ammonium compounds produces satisfactory conditioning effects after the first washing of the hair, but these effects are considerably less pronounced when compared with the sole use of the low-molecular quaternary ammonium salts mentioned initially. Further disadvantages resulting from the use of such polymeric quaternary ammonium compounds are a great accumulation effect when such hair shampoos are used repeatedly and the incomplete ability to form a clear solution in the anionic surfactants which are usually present in hair shampoos.

Reaction products of oxyalkylated tertiary amines with dicarboxylic acids and salts thereof with mineral acids or short-chain carboxylic acids are known from German Offenlegungsschrift No. 3,032,216, the amine-containing polyesters and salts thereof thus prepared having a degree of polymerization of 2 to 50 and being stated to be used in hair shampoos and in hair rinses. For such a use, the polymeric amines and especially their salts have, however, the following disadvantageous properties: they are hard to distribute over the hair; the excess product is difficult to rinse out again and it produces an unpleasant slippery feel on the wet hair thus treated. In addition, amines and amine salts are frequently not satisfactorily tolerated from the dermatological point of view. There is, therefore, a need for substances which do not have the disadvantages mentioned above.

To satisfy this need, the present invention provides quaternary oxalkylated polyesters of the general formula

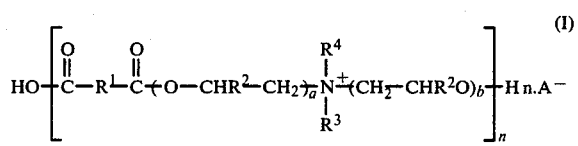

in which $R^1$ is an alkylene radical of the formula $-(CH_2)_m-$ in which m denotes an integer from 1 to 8, this alkylene radical being able to carry, if appropriate, 1 to 2 OH groups, or is a vinylene radical or a p-phenylene radical, $R^2$ is H or $CH_3$, $R^3$ denotes an alkyl radical or alkenyl radical having 8 to 23 carbon atoms, $R^4$ denotes a methyl radical or an ethyl radical or a radical of the formula $-(CH_2CHR^2O)_c-H$ in which c is a whole or fractional number from 1 to 3 and $R^2$ has the above meaning, $A^-$ denotes the anion of a carboxylic acid having 2 to 6 carbon atoms, of a hydroxycarboxylic acid having 2 to 6 carbon atoms and 1 to 3 OH groups, or denotes the methosulfate, ethosulfate, chloride or hydrogen phosphate anion, a and b are identical or different and are a whole or fractional number from 1 to 10, and n is a whole or fractional number which can assume values from 5 to 60.

Preferably, in the formula I, $R^1$ is an alkylene radical of the formula $-(CH_2)_m-$ in which m can assume values from 4 to 8, $R^2$ is H, $R^3$ is an alkyl radical having 16 to 23 carbon atoms, $R^4$ is a radical of the formula $-(CH_2CH_2O)_c-H$ in which c denotes a whole or fractional number from 1 to 3, a and b are identical or different and are a whole or fractional number from 2 to 4, n is a whole or fractional number from 5 to 20 and $A^-$ is the anion of lactic acid, tartaric acid or phosphoric acid.

The compounds of the formula I are obtained by esterifying, with polycondensation, an oxalkylated primary fatty amine of the formula

in which $R^3$, $R^2$, a and b have the meanings indicated in formula I, with a dicarboxylic acid of the formula

in which $R^1$ has the meaning indicated in formula I, the ratio of oxalkylated primary fatty amine to dicarboxylic acid being 0.8:1 to 1:0.8, and by reacting the resulting reaction product with (a) a quaternizing agent selected from the group comprising methyl chloride, dimethyl sulfate or diethyl sulfate, or preferably with (b) ethylene oxide, propylene oxide or mixtures of these two alkylene oxides, in each case together with a carboxylic acid, with phosphoric acid or with hydrochloric acid.

The starting compounds of the formula II are obtained in accordance with known processes by oxalkylating primary fatty amines. A survey of methods for the preparation of this well-known class of compounds is given in Schönfeldt, "Surface Active Ethylene Oxide Adducts", Wissenschaftliche Verlagsgesellschaft, Stuttgart, 1976, pages 70 to 73.

The industrially available products stearylamine or behenylamine are preferred amines which can be oxalkylated to give starting compounds of the formula II. However, it is equally possible, in accordance with the invention, to use other monoamines having a more or less broad distribution of alkyl chains or to use amines having a uniform chain. It is also possible to employ fatty amines, alone or as a mixture, in which the chains contain one or more double bonds, such as the radicals of oleic, elaidic, linoleic or linolenic acid.

Dicarboxylic acids suitable for the esterification are aliphatic dicarboxylic acids having $C_1$— to $C_8$— alkylene groups, such as malonic acid, succinic acid, glutaric acid, adipic acid or sebacic acid, aliphatic dicarboxylic acids which are substituted by 1 to 2 OH groups, such as malic acid, tartronic acid or tartaric acid, and also terephthalic acid, fumaric acid or maleic acid. Aliphatic dicarboxylic acids having 4 to 8 carbon atoms in the alkylene radical, that is to say the homologous series from adipic acid to sebacic acid, are particularly suitable. Derivatives of such dicarboxylic acids, in particular esters and acid halides thereof, are also suitable for the esterification.

The esterification of the compounds of the formula II, which takes place with polycondensation, is effected in accordance with known methods using a dicarboxylic acid of the formula III in fairly high-boiling inert solvents, such as toluene or xylene, or preferably with no solvent in the melt and with blanketing by means of a protective gas. In the case of esterification in a solvent, it is advantageous to choose, as the reaction temperature, the reflux temperature of the reaction mixture and to remove azeotropically the water formed in the reaction. In the case of esterification without a diluent, the water of reaction is distilled off directly from the reaction mixture. The reaction temperatures in this case are 140° to 220° C., preferably 150° to 180° C. An acid catalyst, such as, for example, p-toluenesulfonic acid or hypophosphorous acid, is used in order to accelerate the reaction. The completeness of the reaction is checked by determining the amine number and the acid number. The molar ratio of dicarboxylic acid to compounds of the formula II is varied within a specific ratio. This variation and the degree of conversion in the polycondensation have, as is known, the following effect on the degree of polycondensation $\bar{P}_n$:

$$\bar{P}_n = \frac{1 + q}{1 + q - 2\,pq}$$

in which p denotes the degree of conversion in the polycondensation and q denotes the stoichiometric ratio of dicarboxylic acid to compound of the formula II.

The ratio of oxalkylated fatty amine to dicarboxylic acid is varied within the range 0.8:1 to 1:0.8. It is preferable to use 0.83 to 0.92 mol of the dicarboxylic acid and 1 mol of the oxalkylated amine and to carry out the reaction to almost 100%. The analytical determination of the average degree of polycondensation and thus of the average molecular weight is carried out by HPLC (=high performance liquid chromatography) or HPSEC (=high performance size exclusion chromatography). The quaternization reaction is carried out with ethylene oxide or propylene oxide or mixtures thereof, preferably with ethylene oxide, at a temperature of 80° to 95° C. in a suitable stirred autoclave, and the reaction pressure should preferably not exceed a maximum of 3 bar. In order to form salts, the reaction is carried out with an equivalent amount (corresponding to the number of nitrogen atoms) of one of the carboxylic acids or mineral acids on which the anions $A^-$ defined above are based. Examples of such carboxylic acids are acetic acid or propionic acid each of which can, if appropriate, also carry 1 to 3 hydroxyl groups, such as glycolic acid and lactic acid. The carboxylic acid can also be an optionally OH-substituted dicarboxylic or tricarboxylic acid, such as succinic acid, malonic acid, maleic acid, fumaric acid, malic acid, tartaric acid or citric acid. Finally, suitable mineral acids are orthophosphoric acid or hydrochloric acid. Lactic acid, tartaric acid and orthophosphoric acid are preferred. The degrees of quaternization are determined by two-phase titration of the quaternary product of the formula I with sodium dodecylsulfate at pH 1 to 2 or pH 10.

The quaternization of the polycondensate prepared by the esterification reaction can, however, also be effected at 80° to 90° C. using quaternizing agents such as methyl chloride, dimethyl sulfate or diethyl sulfate, and the pressure should not exceed a maximum of 4 bar. This reaction is preferably carried out in an alkanol having a low carbon chain length. Typical reaction times are within the range from 5 to 12 hours, degrees of quaternization up to 98% being achieved. The determination of the degree of quaternization is carried out as described above.

The following Examples illustrate the preparation of the compounds according to the invention:

EXAMPLE 1

(a) Preparation of a polycondensation product from adipic acid and a stearylamine which has been condensed with 10 mol of ethylene oxide:

564.3 g (0.81 mol) of stearylamine+10 mol of ethylene oxide, 98.6 g (0.67 mol) of adipic acid and 1.7 g of 50% strength by weight hypophosphorous acid are initially placed in a 1 l stirred vessel equipped with a water separator, a gas inlet and heating, the reactants are brought to 180° C. under an atmosphere of nitrogen, and the esterification reaction is continued at this temperature with continuous removal of water. The condensation reaction is found to be virtually complete after a reaction time of 15 hours, by determining the acid number and the amine number.

(b) Quaternization of the resulting polycondensate by means of a carboxylic acid and an alkylene oxide.

377 g (0.45 mol, calculated on the recurring unit) of the polycondensate obtained in accordance with Example 1a) are neutralized with 55.8 g (0.45 mol) of 70% strength lactic acid in the presence of 32.4 g (1.80 mol) of water and 28 g of ethanol, and are quaternized by means of 99.1 g (2.25 mol) of ethylene oxide. The reaction is complete in 7 hours at a temperature of 85° C. and a maximum pressure of 3.0 bar. The result is a liquid which is clear at room temperature. The degree of quaternization of the quaternary polycondensation product is determined from the ratio of acid or alkaline two-phase titration with sodium dodecylsulfate, and is 94%. The reactions indicated in Table 1 below, Examples 2 to 16, which lead to compounds of the formula I in the degrees of quaternization stated can be carried out under the reaction conditions described in Example 1:

almost exclusively only suitable for hair rinses, because of their loss of action in the presence of anionic surfactants, and whereas the polymers mentioned, containing quaternary ammonium groups, cannot be formulated for hair rinses, but only for hair shampoos, inter alia for reasons of inadequate thickening with customary thickeners, the compounds, according to the invention, of the formula I can be used for a very wide variety of purposes in cosmetic care of the hair: they are suitable

TABLE 1

| Example | Acid component | Amine component | % conversion in polycondensation reaction, according to AN[4] | Anion in the quaternary compound | % degree of quaternization |
|---|---|---|---|---|---|
| | Molar ratio | | | | |
| 2 | Adipic acid 1 | Stearylamine + 2 EO[2] 1 | 97 | Lactate | 73 |
| 3 | Adipic acid 0.833 | Stearylamine + 3.5 EO 1 | 99.5 | Lactate | 85 |
| 4 | Adipic acid 0.833 | Stearylamine + 5 EO 1 | 99 | Lactate | 93 |
| 5 | Adipic acid 0.92 | Stearylamine + 10 EO 1 | 99 | Lactate | 84 |
| 6 | Adipic acid 1 | Stearylamine + 10 EO 1 | 98 | Lactate | 84 |
| 7 | Adipic acid 0.833 | Tallow fatty amine + 10 EO 1 | 98.5 | Lactate | 83 |
| 8 | Adipic acid 0.9 | Coconut fatty amine + 5 EO 1 | 99 | Lactate | 82 |
| 9 | Adipic acid 0.9 | Coconut fatty amine + 20 EO 1 | 97.5 | Lactate | 81 |
| 10 | Adipic acid 0.833 | Stearylamine + 3 EO 1 | >99 | Hydrogen phosphate | 92 |
| 11 | Adipic acid 0.833 | Stearylamine + 2 EO + 2 PO[3] 1 | 99 | Lactate | 83 |
| 12 | Adipic acid 0.833 | Stearylamine + 3 EO 1 | >99 | Lactate | 77[1] |
| 13 | Adipic acid 0.833 | Stearylamine + 3 EO 1 | >99 | Chloride | 98 |
| 14 | Adipic acid 0.92 | Stearylamine + 3 EO 1 | | Lactate | 83 |
| 15 | Adipic acid 1 | Stearylamine + 3 EO 0.833 | 97 | Lactate | 80 |
| 16 | Adipic acid 0.833 | Stearylamine + 3 EO 1 | 98.8 | Lactate | 85 |

[1]Quaternization reaction carried out with 80 mol % of lactic acid
[2]EO = ethylene oxide
[3]PO = propylene oxide
[4]AN = acid number

EXAMPLE 17

(a) Preparation of a polycondensation product from adipic acid and a stearylamine which has been subjected to a condensation reaction with 3.5 mol of ethylene oxide:

The ester formation is carried out as described in Example 1 using 412 g (1.0 mol) of stearylamine+3.5 mol of EO, 121.7 g (0.833 mol) of adipic acid and 1.0 g of 50% strength by weight hypophosphorous acid. The conversion is found to be virtually complete after a reaction time of 16 hours, by determining the acid number and the amine number.

(b) Quaternization of the resulting polycondensate by means of methyl chloride.

125 g (0.25 mol of the recurring unit) of the polycondensate obtained in accordance with Example 17a are reacted with 18.7 g (0.37 mol) of methyl chloride in the presence of 130 g of isopropanol. The quaternization is complete after a reaction time of 10 hours at a temperature of 80° C. and a maximum pressure of 5 bar. The degree of quaternization of the product is 90%.

The quaternary oxalkylated polyesters of the formula I according to the invention can be employed universally, especially in cosmetic care of the hair. Whereas the quaternary ammonium salts mentioned above are not only for hair shampoos, but also for hair rinses, hair styling agents, setting lotions and hair dyes and for hair restorers and other preparations for cosmetic care of the hair.

The quaternary oxalkylated polyesters, according to the invention, of the formula I can, however, also be used in other fields of cosmetics, for example in skin care products or lotions or in a very wide variety of types of skin cleansers, but especially in liquid soaps, bar soaps or shower gels, where they impart an agreeable feel to the skin after use.

For the applications mentioned, anionic, nonionic or cationic or zwitterionic surfactants can be added to the compounds, according to the invention, of the formula I. Groups of substances which are particularly suitable for use as nonionic surfactants which are preferentially used in hair after-treating agents are oxalkylated fatty alcohols or alkylphenols, preferably oxalkylated with ethylene oxide or mixtures of ethylene oxide or propylene oxide; polyglycol esters of fatty acids or fatty acid amides; ethylene oxide/propylene oxide block polymers; glycerol esters and polyglycerol esters; sorbitol and sorbitan esters; polyglycol esters of glycerol; oxethylated lanolin derivatives; and alkanolamides and sucrose esters.

The following may be mentioned as anionic surfactants which are particularly suitable for formulating hair shampoos and also other cosmetics: alkylsulfates, alkylpolyether-sulfates; alkylarylpolyether-sulfates; alkylsulfonates; alkylarylsulfonates; α-olefinsulfonates; sulfosuccinic acid derivatives; alkyl glycidyl ether-sulfates and ether-sulfonates; acylalkylolamide sulfates and sulfonates; acylamidopolyglycolether-sulfates and sulfonates; fatty acid taurides; fatty acid isethionates; protein condensates; and fatty acid soaps or fatty acid sarcosides.

Finally, it is also possible to add zwitterionic and cationic surfactants, such as, for example, alkylbetaines and alkylamidobetaines; amine oxides; sulfobetaines and alkylsulfatobetaines; imidazolinium compounds; and quaternary ammonium compounds, particularly those derived from fatty amines.

Customary additives, such as, for example, consistency additives, foam stabilizers, perfume oils, preservatives, anti-dandruff agents, superfatting agents, dyes and sequestering agents can also be added to the compounds, according to the invention, of the formula I to obtain cosmetic preparations for the care of the hair.

The formulations which follow are intended to illustrate possible formulations for cosmetics, without limiting the invention to these Examples (all the percentages given in the following text are percentages by weight):

(a) Clear, medium-viscosity hair shampoo 15.0% of sodium lauryl diglycol ether-sulfate
2.0% of coconut fatty acid diethanolamide
1.5% of the compound from Example 3
0.3% of perfume oil
2.0% of sodium chloride
ad 100.0% of water (b) Hair shampoo in the form of cream 20.0% of sodium coconut fatty acid methyltauride
5.0% of sodium stearic acid methyltauride
2.0% of sodium coconut fatty acid sarcoside
0.4% of perfume oil
2.2% of the compound from Example 2
ad 100.0% of water, preservative and dyestuff (c) Liquid hand cleanser 10.0% of sodium lauryl triglycol ether-sulfate
3.0% of triethanolamine acylaminopolyglycol ether-sulfate
3.0% of coconut-dimethylamine oxide
3.0% of sodium coconut fatty acid isethionate
1.0% of triethylene glycol distearate
0.4% of the compound from Example 2
1.4% of sodium chloride
ad 100.0% of water, preservative and dyestuff (d) Hair rinse concentrate 6.6% of the compound from Example 2
3.0% of cetyl alcohol
1.5% of diglycerol isostearate
ad 100.0% of water, dyestuff and perfume oil (e) Clear hair rinse 4.5% of the compound from Example 3
2.0% of hydroxyethylcellulose
ad 100.0% of water, dyestuff and perfume oil (f) Clear hair rinse concentrate 4.5% of the compound from Example 3
4.0% of the quaternized ether-amine of the formula

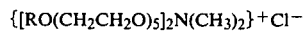

2.0% of hydroxyethylcellulose
ad 100.0% of water, dyestuff and perfume oil (g) Clear hair rinse 6.0% of the compound from Example 3
2.0% of cetyltrimethylammonium chloride
2.0% of hydroxyethylcellulose
ad 100.0% of water, perfume oil and dyestuff (h) Hair cream 0.06% of the compound from Example 1
8.0% of diglycerol tetraglycol stearate
2.0% of glycerol monostearate
15.0% of paraffin oil (highly viscous)
5.0% of isopropyl myristate
3.0% of glycerol
ad 100.0% of water, perfume oil, dyestuff and preservative (i) Liquid setting lotion 0.2% of the compound from Example 2
3.0% of vinylpyrrolidone/vinyl acetate copolymer, ratio 60:40
45.0% of isopropyl alcohol
0.2% of polyethylene glycol 400
ad 100.0% of water and perfume oil (j) Medium-viscosity shower gel 13.0% of sodium lauryl diglycol ether-sulfate
5.0% of triethanolamine acylaminopolyglycol ether-sulfate
2.0% of ethylene glycol distearate
2.2% of the compound from Example 2
0.3% of perfume oil
3.0% of sodium chloride
ad 100.0% of water, preservative and dyestuff (k) Oil-in-water emulsion 0.05% of the compound from Example 2
6.0% of diglycerol tetraglycol stearate
10.0% of paraffin oil, highly viscous
10.0% of isopropyl palmitate
ad 100.0% of water, preservative and perfume oil.

The technical behavior in use of the quaternary oxalkylated polyesters, according to the invention, of the formula I was investigated in vivo on living hair. The pretreatment of the hair approximated to that used in practice and was carried out by washing with a 1% strength solution in water of sodium lauryl diglycol ether-sulfate. The hair was then rinsed out in each case with water at +35° C.

The in vivo test was carried out by the so-called half-head test, i.e. the hair of the head was parted in the middle and in each case 10 ml of a 2% strength aqueous solution or dispersion of the compound according to the invention were distributed over the moist hair of the head by means of a pipette. After a treatment time of 5 minutes, the excess amount was rinsed out by means of 2 l of tap water at +35° C.

Both the antistatic behavior and the facility for combing were then tested by means of a standard comb.

Evaluation was carried out on the basis of the following scheme:
1 = very good
2 = good
3 = moderate
4 = poor
5 = very poor.

The results obtained in the test are shown in Table 2. As can be seen, the compounds according to the invention have both an improved facility for combing when wet and an improved facility for combing when dry and a higher luster, compared with the compound chosen as comparison substance, cetyltrimethylammonium chloride.

The compounds according to the invention produce little foam. When the compounds according to the invention were used in hair shampoos, no so-called accumulating effect was found, which normally has unfavorable effects on the appearance, feel, fullness and luster of the hair, not even after continual use in accordance with practice. The antistatic action is also better than in the case of the comparison products.

TABLE 2

| Product | Manageability of the hair when dry | Manageability of the hair when wet | Luster of the hair |
|---|---|---|---|
| Cetyltrimethylammonium chloride | 3 | 3 | 3 |
| Example 1 | 2 | 3 | 2 |
| Example 2 | 1 | 1 | 1 |
| Example 3 | 1-2 | 1-2 | 1-2 |
| Example 4 | 2 | 2 | 2 |
| Hydroxyethylcellulose, reacted with a trimethyl-ammonium-substituted epoxide in accordance with U.S. Pat. No. 3,472,840 | 3 | 4 | 3 |

We claim:

1. A quaternary oxalkylated polyester of the formula

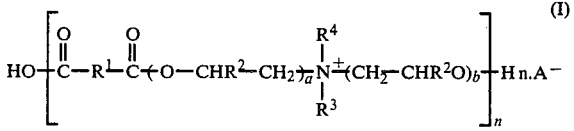

in which
R$^1$ is an alkylene radical of the formula —(CH$_2$)$_m$— in which m denotes an integer from 1 to 8, said alkylene radical being optionally substituted with 1 or 2 OH groups, or is a vinylene radical of a p-phenylene radical,
R$^2$ is H or CH$_3$,
R$^3$ denotes an alkyl radical or alkenyl radical having 8 to 23 carbon atoms,
R$^4$ denotes a methyl radical or an ethyl radical or a radical of the formula —(CH$_2$CHR$^2$O)$_c$—H in which c is a whole or fractional number from 1 to 3 and R$^2$ has the above meaning,
A$^-$ denotes the anion of a carboxylic acid having 2 to 6 carbon atoms, of a hydroxycarboxylic acid having 2 to 6 carbon atoms and 1 to 3 OH groups, or denotes the methosulfate, ethosulfate, chloride or hydrogen phosphate anion,
a and b are identical or different and are a whole or fractional number from 1 to 10, and
n is a whole or fractional number which can assume values from 5 to 60.

2. A quaternary oxalkylated polyester as claimed in claim 1, wherein
R$^1$ is an alkylene radical of the formula —(CH$_2$)$_m$— in which m can assume values from 4 to 8,
R$^2$ is H,
R$^3$ is an alkyl radical having 16 to 23 carbon atoms,
R$^4$ is a radical of the formula —(CH$_2$CH$_2$O)$_c$—H in which c denotes a whole or fractional number from 1 to 3,
a and b are identical or different and are a whole or fractional number from 2 to 4,
n is a whole or fractional number from 5 to 20 and
A$^-$ is the anion of lactic acid, tartaric acid or phosphoric acid.

3. A process for the preparation of quaternary oxalkylated polyesters of the formula I as claimed in claim 1, in which an oxalkylated primary fatty amine of the formula

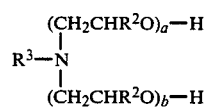

in which R$^3$, R$^2$, a and b have the meanings indicated in formula I, is esterified, with polycondensation, with a dicarboxylic acid of the formula

HOOC—R$^1$—COOH  (III)

in which R$^1$ has the meaning indicated in formula I, the ratio of oxalkylated primary fatty amine to dicarboxylic acid being 0.8:1 to 1:0.8, which comprises reacting the resulting reaction product with ethylene oxide, propylene oxide or mixtures of these two alkylene oxides, in each case together with a carboxylic acid having 2 to 6 carbon atoms, a hydroxycarboxylic acid having 2 to 6 carbon atoms and 1 to 3 OH groups, with phosphoric acid or with hydrochloric acid, said reaction being carried out at 80° to 95° C.

4. The process for the preparation of quaternary oxalkylated polyesters of the formula I as claimed in claim 1, in which an oxalkylated primary fatty amine of the formula

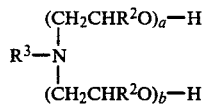
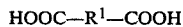

in which R$^3$, R$^2$, a and b have the meanings indicated in formula I, is esterified, with polycondensation, with a dicarboxylic acid of the formula

HOOC—R$^1$—COOH  (III)

in which R$^1$ has the meaning indicated in formula I, the ratio of oxalkylated primary fatty amine to dicarboxylic acid being 0.8:1 to 1:0.8, which comprises reacting the resulting reaction product with a quaternizing agent selected from the group consisting of methyl chloride, dimethyl sulfate and diethyl sulfate, said reaction with the quaternization agent being carried out at 80° to 90° C.

5. A quaternary oxalkylated polyester according to claim 1, wherein $R^1$ is an alkylene radical of the formula $(CH_2)_m$, in which m denotes a whole number from 1 to 8 and wherein said alkylene radical is substituted with 1 or 2 OH-groups.

6. A method for conditioning human hair which comprises shampooing or rinsing the hair with an effective amount of a quaternary oxalkylated polyester of the formula I as claimed in claim 1.

* * * * *